(12) United States Patent
Shankaranarayanan et al.

(10) Patent No.: US 7,953,469 B2
(45) Date of Patent: May 31, 2011

(54) SYSTEM AND METHOD FOR REAL-TIME LOCALIZATION FOR GATED MR IMAGING

(75) Inventors: Ajit Shankaranarayanan, Mountain View, CA (US); Andres Carrillo, Menlo Park, CA (US); Steven D. Wolff, New York, NY (US); Jean Helen Brittain, Menlo Park, CA (US)

(73) Assignee: General Electric Company, Schenectady, NY (US)

( * ) Notice: Subject to any disclaimer, the term of this patent is extended or adjusted under 35 U.S.C. 154(b) by 548 days.

(21) Appl. No.: 12/024,844

(22) Filed: Feb. 1, 2008

(65) Prior Publication Data

US 2008/0132778 A1 Jun. 5, 2008

Related U.S. Application Data

(63) Continuation of application No. 10/904,272, filed on Nov. 2, 2004, now Pat. No. 7,383,074.

(51) Int. Cl.
*A61B 5/05* (2006.01)
(52) U.S. Cl. .................. 600/410; 600/407; 600/413
(58) Field of Classification Search .......... 600/407, 600/410, 413
See application file for complete search history.

(56) References Cited

U.S. PATENT DOCUMENTS

| | | | |
|---|---|---|---|
| 4,710,717 A | 12/1987 | Pelc et al. | |
| 4,830,012 A | 5/1989 | Riederer | |
| 5,329,925 A | 7/1994 | NessAiver | |
| 6,289,232 B1 | 9/2001 | Jakob et al. | |
| 6,434,412 B1* | 8/2002 | Simonetti et al. | 600/410 |
| 6,556,009 B2 | 4/2003 | Kellman et al. | |
| 6,611,701 B2 | 8/2003 | Foo | |
| 6,628,743 B1* | 9/2003 | Drummond et al. | 378/8 |
| 6,801,800 B2 | 10/2004 | Miyazaki et al. | |
| 2002/0171422 A1 | 11/2002 | King | |
| 2006/0100499 A1 | 5/2006 | Shankaranarayanan et al. | |

OTHER PUBLICATIONS

McKenzie et al., Self-Calibrating Parallel Imaging With Automatic Coil Sensitivity Extraction, 2002, Magnetic Resonance in Medicine, 47, pp. 529-538.*
Li et al., "Single-shot Fiesta Single-breath-hold Whole-heart MRI with 4X Parallel Imaging," Proc. Intl. Soc. Mag. Reson. Med. 11, p. 380, 2003.
Nayak et al., "triggered Real-Time MRI and Cardiac Applications," Magnetic Resonance in Medicine, 49:188-192, 2003.
Pruessmann et al., "SENSE: Sensitivity Encoding for Fast MRI," Magnetic Resonance in Medicine, 42:952-962, 1999.
Carrillo et al., "Real-Time Triggered Single R-R CINE Imaging for Whole Heart Coverage in a Breath Hold," GE.
McKenzie et al., "Self-Calibrating Parallel Imaging With Automatic Coil Sensitivity Extraction," Magnetic Resonance in Medicine, 47:529-538, 2002.

(Continued)

*Primary Examiner* — Brian Casler
*Assistant Examiner* — James Kish
(74) *Attorney, Agent, or Firm* — Ziolkowski Patent Solutions Group, SC

(57) ABSTRACT

A system and method for MR imaging is disclosed that includes displaying a series of MR images of an ROI in real-time and localizing a slice within the ROI. The method also includes using a parallel imaging technique to acquire gated MR data from the localized slice and reconstructing a prescribed fixed number of gated MR images of the localized slice.

19 Claims, 3 Drawing Sheets

OTHER PUBLICATIONS

Daniel K. Sodickson, "Tailored Smash Image Reconstructions for Robust In Vivo Parallel MR Imaging," Magnetic Resonance in Medicine, 44:243-251, 2000.

Epstein et al., "Segmented k-Space Fast Cardiac Imaging Using an Echo-Train Readout," Magnetic Resonance in Medicine, 41:609-613, 1999.

* cited by examiner

SYSTEM AND METHOD FOR REAL-TIME LOCALIZATION FOR GATED MR IMAGING

CROSS REFERENCE TO RELATED APPLICATION

The present application is a continuation and claims priority of U.S. patent application Ser. No. 10/904,272 filed Nov. 2, 2004.

BACKGROUND OF THE INVENTION

The present invention relates generally to a magnetic resonance (MR) imaging and, more particularly, to a system and method for real-time, un-gated localization of desired slices for gated MR imaging. The present invention is also capable of producing a prescribed fixed number of images for each R-R period of a cardiac cycle.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", MZ, may be rotated, or "tipped", into the x-y plane to produce a net transverse magnetic moment Mt. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Magnetic resonance imaging is a diagnostic imaging technique commonly used to review, identify, and diagnose pathologies or abnormalities in a scan subject, e.g., medical patient. In particular, MR images of the cardiac region are often used by health care professionals to aid in ventricular assessment. Traditional MR evaluation of ventricular functions often rely on repeated cardiac-gated acquisition of MR data in order to reduce image degradation resulting from the continuous movement of the cardiac region. These gated acquisitions are often performed over multiple cardiac cycles requiring a patient to undergo multiple breath-holds to acquire the requisite MR data to reconstruct the full set of images suitable for diagnosis.

While such cardiac-gated acquisition methods allow the cardiac region to be imaged, the images are susceptible to decreased image quality resulting from variances in breath-hold positions. Specifically, the images often include "misregistration" and may be of poor quality because a patient's breath-hold position differs across acquisition intervals. Furthermore, since cardiac patients suffer from conditions that make reliable cardiac-gated triggering difficult, such as irregular cardiac rhythms, the propensity for degraded images increases significantly with these patients. Additionally, requiring multiple breath-holds of a patient with respiratory problems may be tiring and can increase the sensitivity to differences in the breathhold position. As such, image quality can be affected when imaging a patient having respiratory ailments and/or an irregular cardiac rhythm, as is not uncommon among cardiac patients.

As a result, methods have been developed to reduce image artifacts and misregistration due to cardiac irregularities and/or breath-hold variances. For example, un-gated single-shot imaging techniques have been utilized to reduce misregistration by providing full heart coverage in a single breath-hold. Such methods reduce sensitivity to arrhythmias by acquiring MR data in real-time (i.e. without cardiac gating). However, the acquired data is not synchronized to the cardiac cycle of the patient and the number of acquired images varies from beat-to-beat and, as a result, from location-to-location.

Other, "triggered," real-time MR processes have been developed and implemented to synchronize MR data acquired during real-time imaging to the cardiac cycle. These triggered real-time MR methods rely on automated trigger-based registration methods. Cardiac trigger signals are monitored during continuous real-time scanning and scan parameters are automatically modified in response to each beat within the cardiac cycle. As a result, the acquired data can be synchronized within the cardiac cycle. However, such methods can still produce a variable number of images for each R-R period, which is undesirable for clinical evaluations. That is, these systems are not capable of imaging a prescribed fixed number of cardiac phases for the slice during a given R-R interval. Moreover, many methods are not capable of imaging an entire slice within a single R-R interval of the cardiac cycle. For example, a portion of a first slice is typically imaged during a first R-R interval and then, during a second R-R interval, the remaining portion of the first slice is imaged. As a result, blurring and/or artifacts may result in the reconstructed image. Furthermore, such methods also become sensitive to arrythmias.

It would therefore be desirable to have a system and method capable of reducing the potential for misregistration as well as breath-hold requirements in cardiac imaging. It would also be desirable to have an imaging technique that may be synchronized to the cardiac cycle and yield a prescribed fixed number of images per R-R period. Further, it would be advantageous to allow interactive localization and adjustment of slices and provide full heart coverage along both short and long axis orientations in a single breath-hold.

BRIEF DESCRIPTION OF THE INVENTION

The present invention provides a system and method of interactive MR imaging that overcomes the aforementioned drawbacks. The present invention provides a system and method to perform MR imaging utilizing a real-time imaging technique to prescribe a gated, high-resolution imaging technique. The high-resolution imaging process is localized based on real-time imaging prescriptions and may be synchronized to the cardiac cycle to acquire all data for a given slice during a single R-R period. Using data-sharing image reconstruction techniques, the technique yields a prescribed fixed number of images for each localized slice that represent different time points in the R-R cycle for that slice. Furthermore, real-time localizations of slices allow interactive adjustment of slices such that imaging of the cardiac region may be achieved along both short and long orientations. The combination of a real-time, high frame rate acquisition with a gated high-resolution acquisition reduces the impact of misregistration, and cardiac arrhythmia on image quality.

In accordance with one aspect of the invention, an MRI apparatus is disclosed that includes an MRI system having a plurality of gradient coils positioned about a bore of a magnet to impress a polarizing magnetic field and an RF transceiver system and an RF switch controlled by a pulse module to transmit RF signals to an RF coil assembly to acquire MR images. The MRI apparatus also includes a computer that is programmed to acquire RF coil sensitivity data for a region-of-interest (ROI), un-gated MR data from the ROI, and triggered MR data to partially fill k-space for a slice identified for localization within the ROI. The computer is also programmed to determine MR data for unacquired k-space from the RF coil sensitivity data and the triggered MR data to continue to fill k-space, perform a CINE interpolation of the MR data, and reconstruct high-resolution images of the slice identified for localization.

According to another aspect of the invention, a method of MR imaging moving objects is disclosed that includes displaying a series of MR images in real-time of an ROI having motion therein and localizing at least one slice within the ROI in real-time. The method also includes performing a parallel imaging process to acquire MR data synchronized to a cycle of the motion of the ROI from the at least one localized slice and reconstructing a prescribed fixed number of MR images for each localized slice.

In accordance with another aspect, the invention includes a computer readable storage medium having a computer program stored thereon and representing a set of instructions. When the set of instructions is executed by a computer of an MR apparatus, the computer is caused to perform a real-time acquisition of un-gated MR data from an ROI and receive a selected region within the ROI for localized acquisition of gated MR data. The computer is also caused to acquire gated MR data from the selected region and automatically return to acquisition of un-gated MR data from the ROI after acquisition of the gated MR data. Additionally, the computer is caused to reconstruct a prescribed fixed number of images from the gated MR data.

In accordance with yet another aspect of the invention, an MRI apparatus is disclosed that includes means determining a coil sensitivity of the MRI apparatus, means for acquiring un-gated MR data from a ROI, and means for interrupting the un-gated acquisition to acquire gated MR data for a selected FOV within the ROI. The MRI apparatus also includes means for acquiring less than all data from a given slice to fill less than all k-space during a single R-R period and means for determining data from the coil sensitivity and gated MR data to fill remaining k-space.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The present invention provides a system and method to perform gated MR imaging that may be cardiac-synchronized, which is localized based on real-time imaging prescriptions. Each localized slice is imaged over a single R-R period. In addition, a prescribed fixed number of data sets are derived over each R-R period for each localized slice. By combining real-time MR data acquisition with gated high-resolution acquisition, the impact of misregistration and cardiac arrhythmia on image quality is reduced.

Figure 1:
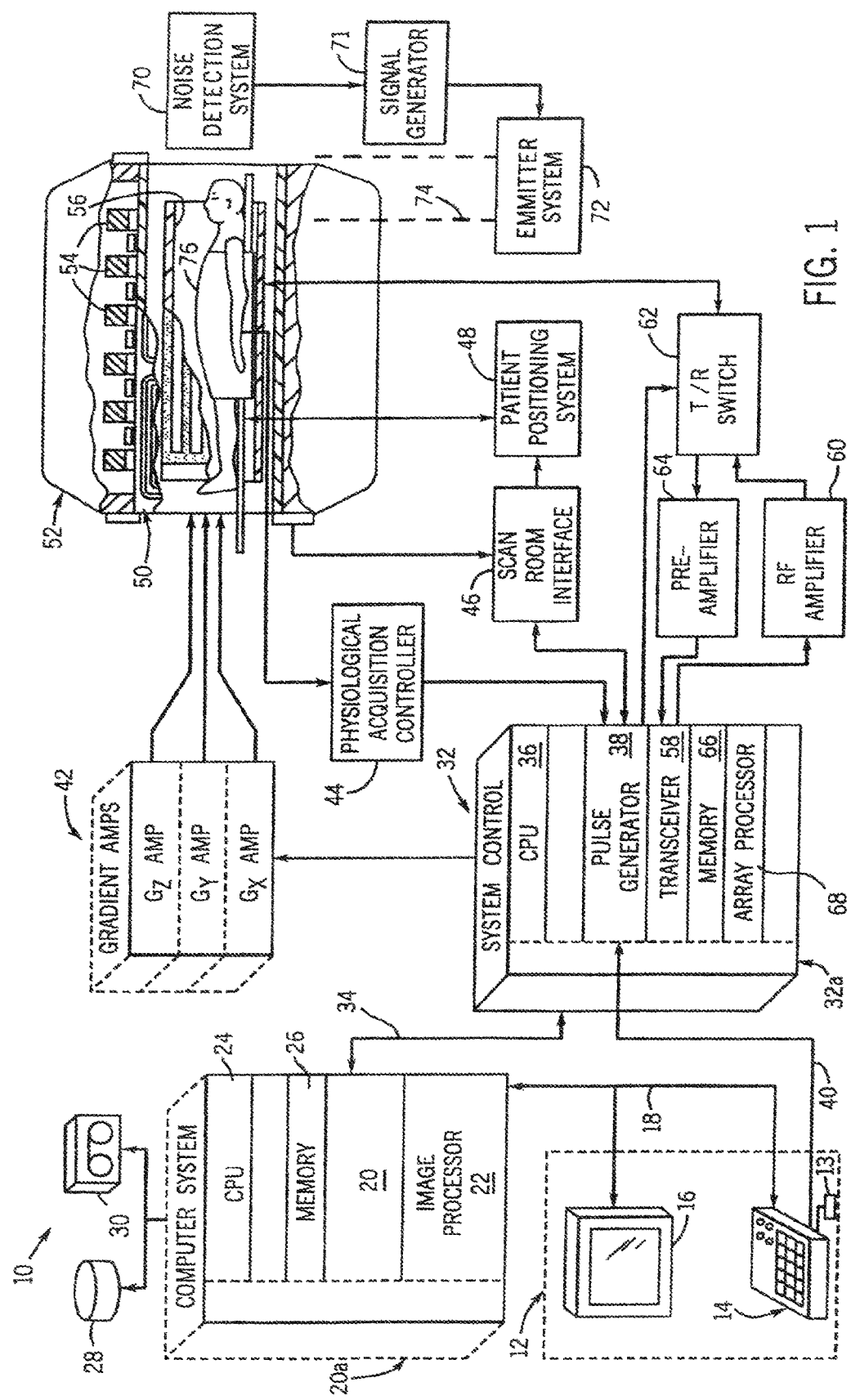
FIG. 1 is a schematic block diagram of an MR imaging system for use with the present invention.

Referring to FIG. 1, the major components of a preferred magnetic resonance imaging (MRI) system 10 incorporating the present invention are shown. The operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly generally designated 50 to produce the magnetic field gradients used for spatially encoding acquired signals. The gradient coil assembly 50 forms part of a magnet assembly 52 which includes a superconducting magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator console 12, this image data may be archived in long term storage, such as on the tape drive 30, or it may be further processed by the image processor 22 and conveyed to the operator console 12 and presented on the display 16.

Figure 2:
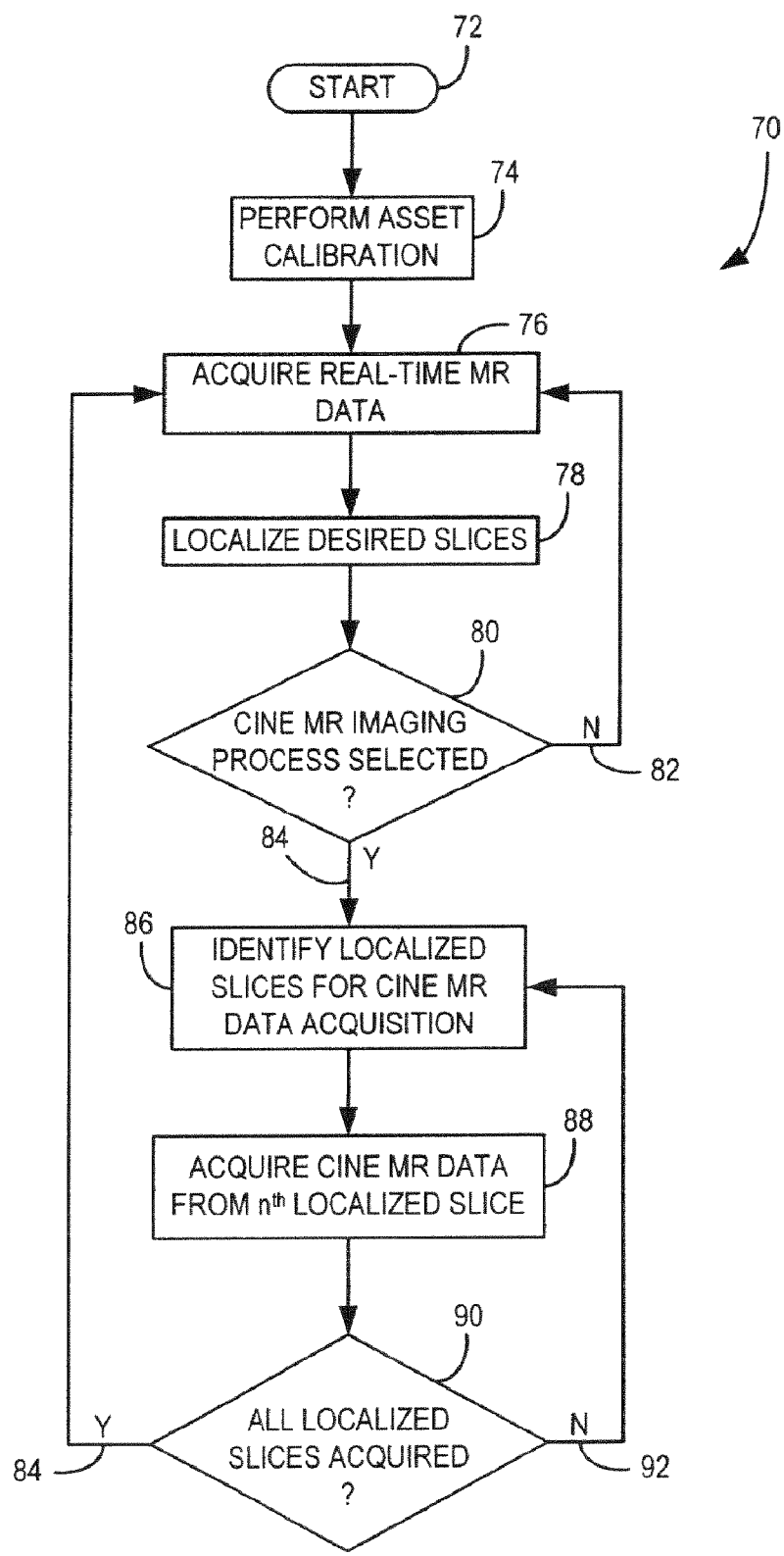
FIG. 2 is a flowchart illustrating the steps of a technique in accordance with the present invention

Referring now to FIG. 2, a flowchart sets forth the steps of a technique 70 to be utilized with the MRI system 10, of FIG. 1. As will be described, the technique combines the benefits of real-time imaging, for rapid localization and arbitrary slice definition, with gated imaging. Specifically, the technique 70 combines real-time imaging processes and CINE imaging processes that are gated in order to support the synchronization of acquired data within the cardiac cycle or other cyclical movement patterns. That is, commencement of the CINE imaging process is gated to obtain full heart coverage in a single breath-hold and acquisition of each slice in a single R-R interval.

In accordance with a preferred embodiment of the invention, the CINE imaging process utilizes a parallel imaging approach, such as Array Spatial Sensitivity Encoding Technique (ASSET) or Sensitivity Encoding (SENSE), with an appropriate acquisition acceleration factor. Specifically, the technique includes a determination of RF coil sensitivity for a ROI. As will be described, the RF coil sensitivity data is used to continue to fill any unfilled k-space. Therefore, the technique 70 begins 72 by performing ASSET calibrations 74 in preparation for the CINE imaging process that, as will be described, follows localization of desired slices through a real-time imaging process 76.

After ASSET calibrations have been completed 74, real-time, or un-gated, MR data is acquired 76 by performing a real-time MR imaging process. Images reconstructed from the acquired real-time MR data 76 are displayed in real-time to enable localization of desired slices 78 either automatically or in response to a user input. Accordingly, the localizations of desired slices are performed in real-time 76. As such, multiple short or long axis, two chamber and four chamber, views may be localized to provide whole heart coverage. Additionally, it is contemplated that during the real-time imaging process 76, real-time adjustment of imaging parameters is permitted. As such, an operator may adjust a slice thickness, flip angle, and/or field-of-view (FOV) in real-time.

After a slice has been localized 78, the MR scanner is controlled to await a CINE initialization command or input. In this regard, if a CINE imaging process has not yet been initiated 82, the acquisition of real-time MR data 74 continues which allow for further identification and selection of pieces for localization. However, if a CINE MR imaging process has been selected 84, a switch is made from data acquisition according to the real-time MR process 76 to data acquisition according to a CINE or other gated data acquisition process.

It is contemplated that, following localization 78, a single button push or other user-input instantaneously switches the data acquisition process from a real-time mode 76 to a 2D high-resolution gated CINE mode.

After a CINE MR imaging process has been selected 84, an identification of the slices previously localized during real-time MR data acquisition is made for the CINE data acquisition 86. Each slice is imaged over a single R-R period and reconstructed to generate a fixed number of images per slice. It is recognized that while the number of images per slice is fixed, the specific number of images may be prescribed by an operator to designate the specific fixed quantity of images. During the high-resolution CINE acquisition 88, k-space is partially filled with the triggered MR data. The RF coil sensitivity data derived during the ASSET calibrations 74 is then used to extrapolate data to fill the unacquired k-space.

It is contemplated that the multiple localized slices may be arranged in a sequence and imaged in a single breath-hold. As such, as will be described, CINE data acquisition may be performed sequentially from the first to the $n^{th}$ slice. Once identified/sequenced, CINE imaging commences to sequentially acquire data from each of the slices localized during the real-time imaging process 88. Contextual information including center frequency, transmit/receive gains, and shim values is automatically shared between the real-time and CINE acquisitions.

Once all data from a localized slice has been acquired 88, a check is made to determine whether all slices previously localized during real-time MR data acquisition have been imaged during the CINE imaging process 90. That is, a verification step is carried to confirm that all slices localized during the real-time imaging process 74 have been sequentially acquired using the CINE imaging process 88. The resulting CINE image loops are automatically saved to a separate series of data. If all localized slices have not yet been imaged 92, the remaining localized slices are identified 86 and imaged 88. Again, all data for a given slice is acquired in a single R-R period and reconstructed to produce a prescribed fixed number of images for each R-R period and slice. Accordingly, each slice localized during the real-time imaging process 78 is sequentially imaged using the CINE imaging process 88. However, after the CINE acquisition is complete 94, the system immediately returns to the continuous acquisition, reconstruction, and display of real-time interactive images 76. Accordingly, the real-time images are preferably displayed on a graphical user interface (GUI) allows interactive localization and adjustment of slices of interest by a user.

By enabling flexible inter-sequence switching in cardiac MR evaluation, the above-described technique improves the quality, accuracy, and efficiency of cardiac MR evaluation. The combination of a real-time, high-frame-rate acquisition with a guided, high-resolution, single-breath-hold CINE acquisition overcomes both slice positioning and resolution issues while minimizing the effects of cardiac arrhythmia and misregistration.

It is contemplated that the real-time imaging process may use the same acquisition matrix as the CINE imaging process but without using a parallel imaging approach to acquire a lower resolution image. However, it is also contemplated that the real-time imaging process may use parallel imaging, such as ASSET, to maintain a similar or more similar spatial resolution to the CINE imaging process. As such, it is contemplated that k-space for the data acquired during the real-time imaging process may be dimensionally equivalent to k-space for the data acquired during the CINE imaging process or may be reduced for increased efficiency.

Figure 3:
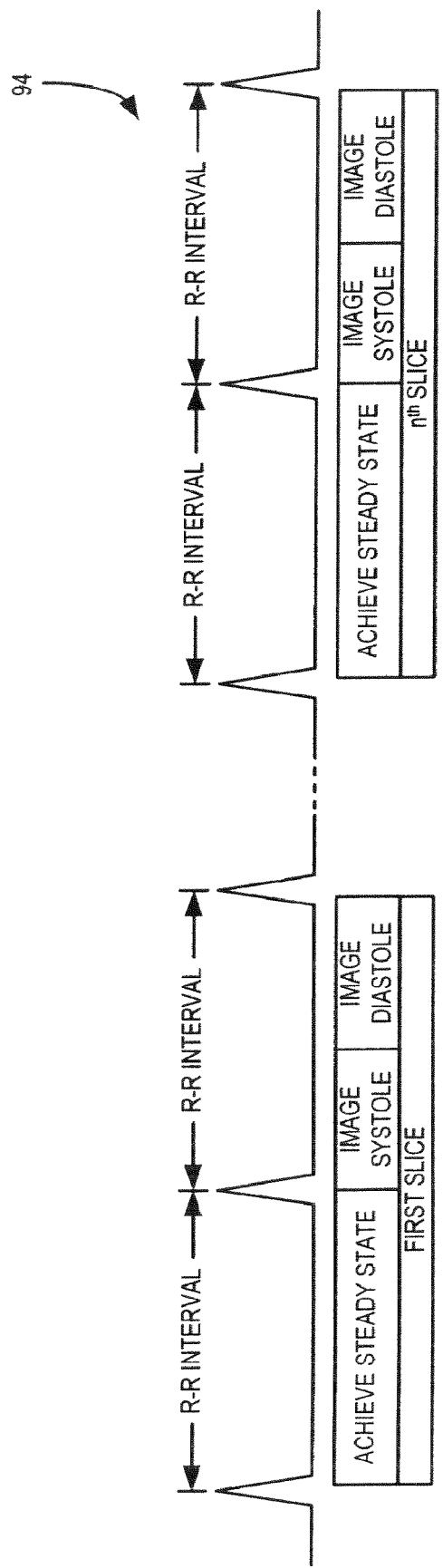
FIG. 3 is a timing diagram of a data acquisition sequence within a cardiac cycle.

As stated above, the above-described technique allows real-time, un-gated localization of desired slices followed by an immediate switch to a 2D, cardiac-gated, high-resolution CINE acquisition. Referring now to FIG. 3, a data acquisition 94, in accordance with the above-described technique, is schematically shown. Specifically, for each slice location ($1^{st}$-$n^{th}$), one R-R interval is used to achieve a steady state and the following R-R interval is used to image the slice. It is contemplated that methods for rapidly achieving steady-state may make the extra R-R interval unnecessary. Under either approach, the CINE imaging process acquires all data for one slice ($1^{st}$-$n^{th}$) in a single R-R interval and provides full heart coverage (systole and diastole) and can provide both short and long axis orientations within a single breath-hold. Data is acquired that is retrospectively interpolated to reconstruct the prescribed number of phases per location. Accordingly, this technique significantly reduces sensitivity to arrhythmia since all data for a given slice is acquired in a single R-R period.

Furthermore, the technique reduces susceptibility to misregistration since all slices are acquired sequentially ($1^{st}$-$n^{th}$) in a single breathold. If desired, the user can specify the order in which the slices are to be acquired. The technique allows interactive localization and adjustment of the slices of interest and streamlines display and analysis of the acquired images since the retrospective CINE interpolation produces a prescribed fixed number of images for each R-R period.

Therefore, the acquisition of each slice is completed within a single R-R interval, making it less sensitive to arrhythmias, while slice progression is synchronized with cardiac triggers. By performing real-time localization, the prescription of multiple non-parallel slices can be achieved, which enhances the efficiency of imaging studies. It should be recognized that the technique can be easily extended to the examination of valvular morphology, which requires increased precision in slice selection and higher spatial and temporal resolutions. In addition, the technique would also be compatible with self-encoded parallel imaging methods.

Therefore, the present invention includes an MRI apparatus that includes an MRI system having a plurality of gradient coils positioned about a bore of a magnet to impress a polarizing magnetic field and an RF transceiver system and an RF switch controlled by a pulse module to transmit RF signals to an RF coil assembly to acquire MR images. The MRI apparatus also includes a computer that is programmed to acquire RF coil sensitivity data for a ROI, un-gated MR data from the ROI, and triggered MR data to partially fill k-space for a slice identified for localization within the ROI. The computer is also programmed to determine MR data for unacquired k-space from the RF coil sensitivity data and the triggered MR data to continue to fill k-space, perform a CINE interpolation of the MR data, and reconstruct high-resolution images of the slice identified for localization.

In another embodiment of the present invention, a method of MR imaging moving objects includes displaying a series of MR images in real-time of an ROI having motion therein and localizing at least one slice within the ROI in real-time. The method also includes performing a parallel imaging process to acquire MR data synchronized to a cycle of the motion of the ROI from the at least one localized slice and reconstructing a prescribed fixed number of MR images for each localized slice.

Another embodiment of the present invention includes a computer readable storage medium having a computer program stored thereon and representing a set of instructions. When the set of instructions is executed by a computer of an MR apparatus, the computer is caused to perform a real-time acquisition of un-gated MR data from an ROI and receive a selected region within the ROI for localized acquisition of gated MR data. The computer is also caused to acquire gated MR data from the selected region and automatically return to acquisition of un-gated MR data from the ROI after acquisition of the gated MR data. The computer is caused to reconstruct a prescribed fixed number of images from the gated MR data.

A further embodiment of the present invention has an MRI apparatus that includes means determining a coil sensitivity of the MRI apparatus, means for acquiring un-gated MR data from a ROI, and means for interrupting the un-gated acquisition to acquire gated MR data for a selected FOV within the ROI. The MRI apparatus also includes means for acquiring less than all data from a given slice to fill less than all k-space during a single R-R period and means for determining data from the coil sensitivity and gated MR data to fill remaining k-space.

The present invention has been described in terms of the preferred embodiment, and it is recognized that equivalents, alternatives, and modifications, aside from those expressly stated, are possible and within the scope of the appending claims.

What is claimed is:

1. An MRI apparatus to acquire images comprising:
   a MRI system having a plurality of gradient coils positioned about a bore of a magnet to impress a polarizing magnetic field and an RF transceiver system and an RF switch controlled by a pulse module to transmit RF signals to an RF coil assembly to acquire MR images; and
   a computer programmed to:
      acquire RF coil sensitivity data for a region-of-interest (ROI);
      acquire un-gated MR data from the ROI;
      reconstruct a series of real-time MR images from the acquired un-gated MR data;
      identify at least one slice from at least one image of the series of real-time MR images to obtain a slice identified for localization within the ROI;
      acquire triggered MR data from the at least one slice to partially fill k-space for the slice identified for localization;
      determine MR data for unacquired k-space from the RF coil sensitivity data and the triggered MR data to continue to fill k-space;
      perform a CINE interpolation of the triggered MR data; and
      reconstruct high-resolution images of the slice identified for localization.

2. The MRI apparatus of claim 1 wherein the computer is further programmed to acquire all the triggered MR data for the given slice within a single R-R interval.

3. The MRI apparatus of claim 2 wherein the computer is further programmed to acquire the triggered MR data in an R-R interval immediately following an R-R interval used for steady-state inducement.

4. The MRI apparatus of claim 1 wherein the computer is further programmed to perform an ASSET acquisition to acquire the triggered MR data and determine the MR data for the unacquired k-space.

5. The MRI apparatus of claim 1 wherein the computer is further configured to perform self-encoded parallel imaging to acquire the triggered MR data.

6. The MRI apparatus of claim 1 wherein the computer is further programmed to acquire triggered MR data for all the slices identified for localization within a single breath-hold, wherein the triggered MR data is triggered by a cardiac cycle of an imaging subject.

7. The MRI apparatus of claim 1 wherein the computer is further caused to retrospectively interpolate the triggered MR data and reconstruct a prescribed fixed number of images of the slice identified for localization.

8. The MRI apparatus of claim 1 wherein the computer is further caused to automatically return to the acquisition of the un-gated MR data following the acquisition of triggered MR data.

9. The MRI apparatus of claim 1 wherein the computer is further caused to acquire the triggered MR data with a center frequency, transmit/receive gains, and shim values used to acquire the un-gated MR data.

10. The MRI apparatus of claim 1 wherein the computer is programmed to automatically identify the at least one slice to cover a whole heart of a medical patient.

11. A method of MR imaging moving objects comprising:
　acquiring un-gated MR data for reconstruction into a series of real-time MR images of an ROI having motion therein;
　displaying the series of MR images in real-time of the ROI having motion therein;
　localizing at least one slice within the ROI in real-time;
　performing a parallel imaging process to acquire MR data synchronized to a cycle of the motion of the ROI from the at least one localized slice; and
　reconstructing a prescribed fixed number of MR images for the at least one localized slice.

12. The method of claim 11 further comprising acquiring the MR data in a single R-R interval.

13. The method of claim 12 further comprising inducing steady-state conditions in the localized slice in a calibration R-R interval and acquiring the MR data in an imaging R-R interval, the calibration R-R interval immediately preceding the imaging R-R interval.

14. The method of claim 11 further comprising acquiring MR data from the at least one localized slice within a single breath-hold.

15. The method of claim 14 further comprising acquiring the fixed number of MR images per R-R interval of a measured cardiac cycle.

16. The method of claim 11 further comprising allowing interactive selection of one or more slices for localization by a user on a GUI.

17. The method of claim 11 further comprising automatically returning to the continuous displaying of real-time MR images of the ROI following reconstruction of the prescribed fixed number of MR images for the at least one localized slice.

18. The method of claim 11 further comprising acquiring the un-gated MR data and MR data synchronized to a cycle of the motion of the ROI with a phased-array coil arrangement.

19. The method of claim 11 further comprising acquiring the un-gated MR data with an ASSET acquisition; and
　carrying out the ASSET acquisition at a spatial resolution equivalent to that used to acquire the MR data synchronized to a cycle of the motion of the ROI.

* * * * *